(12) United States Patent
Watson

(10) Patent No.: US 10,285,361 B2
(45) Date of Patent: May 14, 2019

(54) HYBRID ONION VARIETY NUN 07206 ON

(71) Applicant: Nunhems B.V., Nunhem (NE)

(72) Inventor: Rick Watson, Silverton, OR (US)

(73) Assignee: NUNHEMS B.V., Nunhem (NL)

(*) Notice: Subject to any disclaimer, the term of this patent is extended or adjusted under 35 U.S.C. 154(b) by 0 days.

(21) Appl. No.: 15/425,012

(22) Filed: Feb. 6, 2017

(65) Prior Publication Data

US 2017/0142922 A1    May 25, 2017

Related U.S. Application Data

(60) Provisional application No. 62/299,031, filed on Feb. 24, 2016.

(51) Int. Cl.
*A01H 5/06* (2018.01)
*A01H 6/04* (2018.01)

(52) U.S. Cl.
CPC .............. *A01H 6/045* (2018.05); *A01H 5/06* (2013.01)

(58) Field of Classification Search
None
See application file for complete search history.

(56) References Cited

U.S. PATENT DOCUMENTS

| 2009/0193545 A1 | 7/2009 | Watson |
| 2011/0041217 A1 | 2/2011 | Watson |

FOREIGN PATENT DOCUMENTS

| WO | 2013182646 A1 | 12/2013 |
| WO | 2014076249 A1 | 5/2014 |

OTHER PUBLICATIONS

Conner et al. Effects of essential oils from plants on growth of food spoilage yeasts. (1984) J. of Food Science; vol. 49, pp. 429-434.*
McCollum, G. D. Chromosome behavior and sterility of hybrids between the common onion Allium Cepa, and the related wild A. oschanininii (1974) Euphytica; vol. 23; pp. 699-709.*
Kamenetsky, R. Vegetative propagation of species of genus *Allium* L. (1993) Water Science and Technology; vol. 27; pp. 511-517.*
Simon, P. W. Genetic analysis of pungency and soluble solids in long-storage onions. (1995) Euphytica; vol. 82; pp. 1-8.*
Wednozy et al. Progress in doubled haploid technology in higher plants. (2009) Chapter 1 in Advances in Haploid Production in Higher Plants; A. Touraev et al. (editors); Springer Science.*
Acquaah, Principles of Plant Genetics and Breeding, 2007, Blackwell Publishing, ISBN-13: 978-1-4051-3646-4.
US Department of Agriculture, Agricultural Marketing Service, Objective Description of Variety Onion (*Allium cepa* L.) http://www.ams.usda.gov/AMSv1.0/getfile?dDocName=STELDEV3003776; updated Jun. 2015.
UPOV, Guidelines for the Conduct of Tests for Distinctness, Uniformity and Stability, TG/46/7 (Geneva 2008), http://www.upov.int/edocs/tgdocs/en/tg046.pdf.
Dunstan and Short, "Improved Growth of Tissue Cultures of the Onion, Allium cepa", Physiol. Plant, 1977, vol. 41, pp. 70-72.
Wijnker et al., "Hybrid recreation by reverse breeding in *Arabidopsis thaliana*", Nature Protocols, 2014, vol. 9:4, pp. 761-772.
Vos et al., "AFLP: a new technique for DNA fingerprinting", Nucleic Acids Research, 1995, vol. 23:21, pp. 4407-4414.
Ince et al., "Genetic Relationships Within and Between *Capsicum* Species", Biochem. Genet., 2010, vol. 48, pp. 83-95, DOI 10.1007/s10528-009-9297-4.
Vidavsky and Czosnek, "Tomato Breeding Lines Resistant and Tolerant to Tomato Yellow Leaf Curl Virus Issued from Lycopersicon hirsutum", Phytopathology, 1998, vol. 88, No. 9, pp. 910-914.

* cited by examiner

*Primary Examiner* — Cathy Kingdon Worley
(74) *Attorney, Agent, or Firm* — Arent Fox LLP

(57) ABSTRACT

The invention provides a new and distinct hybrid variety of onion, NUN 7206 ON. The invention also provides for parts of such plants, such as bulbs. The invention further provides for methods of making and using hybrid variety NUN 7206 ON.

14 Claims, No Drawings

HYBRID ONION VARIETY NUN 07206 ON

CROSS-REFERENCE TO RELATED APPLICATION

This application claims the benefit of U.S. Provisional Application Ser. No. 62/299,031, filed Feb. 24, 2016, the contents of which are herein incorporated by reference in their entirety.

FIELD OF THE INVENTION

The present invention relates to the field of plant breeding and, more specifically, to the development of onion variety NUN 7206 ON (also designated as NUN 07206 ONL or NUN 07206 ON, or NUN 7206 ON, or NUN 07206 or NUN 07206 F1 or NUN 07206 hybrid or 07206 ONL or Airoso). The invention further relates to a vegetative reproduction of NUN 7206 ON, methods for in vitro tissue culture of NUN 7206 ON, an explant and also to phenotypic variants of NUN 7206 ON. The invention further relates to methods of producing bulbs or bulblets of NUN 7206 ON.

The goal of vegetable breeding is to combine various desirable traits in a single variety/hybrid. Such desirable traits may include greater yield, resistance to insects or pests, tolerance to heat and drought, desired earliness, better agronomic quality, higher nutritional value, growth rate and bulb properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype.

Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential. One crop species which has been subject to such breeding programs and is of particular value is the onion.

Onions belong to the lily family, Amaryllidaceae, and the genus *Allium*. *Allium* comprises a group of perennial herbs having bulbous, onion-scented underground leaves, commonly known as onion bulbs, including such commonly cultivated crops as garlic, chives, and shallots. It also includes ornamental species grown for their flowers.

Onions are an important vegetable world-wide, ranking second among all vegetables in economic importance with an estimated production of over 80 million tons in 2012 (FAOSTAT). The onion is also one of the oldest cultivated vegetables in history. In general, the bulb is harvested and eaten. The common garden onions belong to the species *Allium cepa*. Onions are classified in numerous ways, by basic use, flavor, color, shape of the bulb, and day length. Onions come in white, yellow, and red colors. The bulb may be rounded, flattened, or tapering cylindrical.

Commercial onions include "storage onions", "fresh onions", "pearl or mini onions", and "green onions". "Fresh onions" tend to have a lighter color with a thin skin, a milder, sweeter flavor, and must be eaten fresh as they do not store well. These onions are available in red, yellow, and white colors.

Storage onions are available from harvest, which is at the beginning of August, and are stored and available throughout the winter months up to about March. Storage onions have a darker skin that is thicker than that of a fresh onion. They are also known for intense, pungent flavor, higher percentage of solids and desirable cooking characteristics. These onions are also available in red, yellow and white colors. Not all long day length type (long day type) onions are suitable for storage. A true storage onion is one that can be harvested in late summer or fall, and stored, under proper conditions, until the spring, when the fresh onion crop is again available.

"Spanish onion", "Spanish onions", or "Spanish type" are terms applied to various long-day onions, generally yellow, though some white, and generally varieties that are large and globe-shaped. Spanish onion is commonly applied to various long day type onions of the type grown in western states of the United States (California, Idaho, Oregon, Washington, Colorado) with a bulb size averaging 300-700 grams (g) (typically over 3 inches up to 4 inches but also up to 5 inches in diameter for bulbs classified as "colossal").

Onion varieties initiate bulbing when both the temperature and a minimum number of daylight hours reach certain levels. When onions are first planted, they initially develop their vegetative growth, with no sign of bulb formation until the proper day length for that onion variety triggers the signal to the plant to stop producing above ground vegetative growth and start forming a bulb. Onions are thus sensitive to the hours of daylight and darkness they receive, and for most varieties it is only when the specific combination of daylight and darkness is reached, that the bulb starts to form. Onions are therefore classified by the degree of day length that will initiate bulb formation. Onions are described as short-, intermediate-, and long-day length types. Short day means that bulbing will initiate at 11 to 12 hours of daylight. Intermediate day is used for onions bulbing at 12 to about 14 hours of daylight. Long day onions require about 14 or more hours of daylight for bulb formation to start.

Growers producing onions in more northerly climates plant long-day length onions. Daylight length varies greatly with latitude, and at higher latitudes long-day onions will produce sufficient top growth before the day length triggers bulbing to produce a large bulb. A short-day onion grown in the North (higher latitudes) will bulb too early and produce relatively small bulbs.

Short day onions are preferred for southern areas such as southern Texas, southern California and Mexico. If a long day type onion is planted in such a short day climate, it may never experience enough day length to trigger the bulbing process.

Onions are also classified on flavor, with the common designations of sweet, mild, and pungent. The flavor of the onion is a result of both the type of onion and the growing conditions. For instance, soils containing a high amount of sulfur result in more pungent flavored onions. Sweetness in onions is caused by the sugars glucose, fructose and sucrose. Onions also contain polymers of fructose called fructans. Onion cultivars differ quite markedly in the relative amounts of sucrose, glucose, fructose and fructans which they contain. They also differ in sugars according to length of storage and location in the bulb. Short day cultivars, which are poor storers, tend to have higher levels of sucrose, fructose and glucose, but hardly any of the fructans. In contrast, long day type cultivars and intermediate storage cultivars such as Pukekohe Longkeeper have less sucrose, glucose and fructose and higher amounts of fructans.

Short day varieties do not keep well in storage conditions, and the pungency of short day varieties can climb considerably during storage. Present production in North America and Europe allows harvest of short day onions from mild winter regions from November through April. Long day onions are available fresh in the late summer and as storage onions from September through March, or even year round, have not been available in low pungency varieties (with the exception of U.S. patent application Ser. No. 12/861,740 which is based on patent application Ser. No. 12/020,360). Sweet onions must be imported from the southern hemisphere to fill the gap in sweet onion production (November-February). In the United States, regions like Georgia and Texas produce short day onions from March to June, while low pungency onions available from November to February are short day onions, produced in the southern hemisphere.

The use of a type of onion is depending on a customer's preference for taste, aroma, appearance and color of an onion. There is thus a need for new short day onions with new appearance and color properties.

SUMMARY OF THE INVENTION

In one aspect of the invention, a seed of onion variety NUN 7206 ON is provided, wherein a representative sample of said seed has been deposited under Accession Number NCIMB 42143. The onion seed of the invention may be provided as an essentially homogeneous population of onion seed. Therefore, seed of the invention may be defined as forming at least about 97% of the total seed, including at least about 98%, 99% or more of the seed. The population of onion seed may be particularly defined as being essentially free from other seed. The seed population may be separately grown to provide an essentially homogeneous population of onion plants according to the invention. Also encompassed are a plant grown from a seed of onion variety NUN 7206 ON and a plant part thereof.

In another aspect the invention provides for a hybrid variety of Allium cepa called NUN 7206 ON. The invention also provides for a seed or a plurality of seeds of the new variety, a plant produced from growing the seed of the new variety NUN 7206 ON, and a progeny of any of these. Especially, a progeny retaining all or all but one, two or three of the "distinguishing characteristics" or all or all but one, two or three of the "morphological and physiological characteristics" or essentially all physiological and morphological characteristics of NUN 7206 ON referred to herein, are encompassed herein as well as methods for producing these.

In one aspect, such progeny have all the physiological and morphological characteristics of onion variety NUN 7206 ON when grown under the same environmental conditions. In another aspect such progeny have all or all but one, two or three the physiological and morphological characteristics as listed in Table 1 and/or 2 and/or 3 as onion variety NUN 7206 ON when measured under the same environmental conditions (i.e. evaluated at significance levels of 1%, 5% or 10% significance, which can also be expressed as a p value).

In another aspect a plant of the invention or said progeny plants has/have 3, 4, 5, 6, 7, 8, or more or all of the distinguishing characteristics: 1) average bulb diameter; 2) average plant height; 3) average leaf length; 4) typical bulb scale retention; 5) typical leaf bloom; 6) average column height; 7) average column height; 8) average scape length; 9) average scape diameter; and 10) average bulb weight, in addition to 3, 4, 5, 6, 7, 8, or more, or all of the other (average) characteristics as listed in Table 1 and/or 2 and/or 3. NUN 7206 ON is a long day onion.

Further, an onion bulb produced on a plant grown from these seeds is provided.

In yet another embodiment of the invention, a plant having one, two or three physiological and/or morphological characteristics which are different from those of NUN 7206 ON and which otherwise has all the physiological and morphological characteristics of NUN 7206 ON as listed in Table 1 and/or 2 and/or 3, wherein a representative sample of seed of variety NUN 7206 ON has been deposited under Accession Number NCIMB 42143, is provided.

Further, a vegetatively propagated plant of variety NUN 7206 ON, or a part thereof, is provided having all or all but one, two or three of the morphological and physiological characteristics of NUN 7206 ON when grown under the same environmental conditions.

Also a plant part derived from variety NUN 7206 ON is provided, wherein said plant part is selected from the group consisting of: a bulb, a harvested bulb, a part of a bulb, a bulblet, a part of a bulblet, a scale, a part of a scale, a leaf, a part of a leaf, pollen, an ovule, a cell, a petiole, a shoot or a part thereof, a stem or a part thereof, a root or a part thereof, a root tip, a cutting, a seed, a part of a seed, seedcoat or another maternal tissue which is part of a seed grown on NUN 7206 ON, hypocotyl, cotyledon, a pistil, an anther, and a flower or a part thereof. Bulbs are particularly important plant parts. In yet another aspect, a seed of NUN 7206 ON is provided. In still another aspect, a seed growing or grown on a plant of NUN 7206 ON are provided.

Definitions

"Onion plant" or "onion" is a plant of genus Allium or a part thereof (e.g. a bulb). Onion includes, e.g., *Allium aggregatum* (e.g., chalottes and potato onion), *Allium cepa* and *Allium fistulosum*, as well as crossbreds thereof, and hybrids such as *Allium xproliferum*, *Allium xwakegi*, and the triploid onion *Allium xcornutum*. The most commonly eaten part of an onion is the bulb or bulblet.

"Biennial plant" means that *Allium cepa* L. produces a bulb in the first season and seeds in the second.

"Cultivated onion" refers to plants of *Allium*, i.e. varieties, breeding lines or cultivars of the species *Allium cepa* as well as crossbreds with *Allium aggregatum* and *Allium fistulosum*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of *Allium* and related species.

The terms "onion plant designated NUN 7206 ON", "NUN 07206", "NUN 07206 F1", "NUN 07206 hybrid", "07206 ONL" or "variety designated 07206 ONL" are used interchangeably herein and refer to a onion plant of variety NUN 7206 ON, representative seed of which having been deposited under Accession Number NCIMB 42143.

A "seed of NUN 7206 ON" refers to an F1 hybrid seed represented by the deposit with Accession Number NCIMB 42143. It contains an embryo of NUN 7206 ON, or a "1 hybrid embryo". When said seed is planted, it grows into a plant of NUN 7206 ON.

A "seed grown on NUN 7206 ON" refers to a seed grown on a mature plant of NUN 7206 ON or inside a fruit of NUN 7206 ON. The "seed grown on NUN 7206 ON" contains tissues and DNA of the maternal parent, NUN 7206 ON. The "seed grown on NUN 7206 ON" contains an F2 embryo. When said seed is planted, it grows into a first generation progeny plant of NUN 7206 ON.

"Tissue culture" refers to a composition comprising isolated cells of the same or a different type or a collection of such cells organized into parts of a plant. Tissue culture of various tissues of onion and regeneration of plants therefrom is well known and widely published (see, e.g., Dunstan and Short (1977) Physiol, Plant, 41: 70-72.; Pike and Yoo, Scientia Horticulturae, 45 (1990) 31-36). Similarly, the skilled person is well-aware how to prepare a "cell culture".

"UPOV descriptors" are the plant variety descriptors described for onion in the "Guidelines for the Conduct of Tests for Distinctness, Uniformity and Stability", TG/46/7 (Geneva 2009, revised 2015), as published by UPOV (International Union for the Protection of New Varieties and Plants, available on the world wide web at upov.int) and which can be downloaded from the world wide web at edocs/tgdocs/en/tg046.pdf and is herein incorporated by reference in its entirety.

"USDA descriptors" are the plant variety descriptors for onion (*Allium cepa*) as published by the US Department of Agriculture, Agricultural Marketing Service, Plant Variety Protection Office, Beltsville, Md. 20705 (available on the world wide web at ams usda.gov) and which can be downloaded from the world wide web at /sites/default/files/media/16-Onion.pdf.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE.

As used herein, the term "plant" includes the whole plant or any part or derivative thereof, preferably having the same genetic makeup as the plant from which it is obtained, such as a plant organ (e.g. harvested or non-harvested bulbs), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, or parts of a plant (e.g. harvested tissues or organs), such as a bulb, a harvested bulb, a part of a bulb, a bulblet, a part of a bulblet, a scale, a part of a scale, a leaf, a part of a leaf, pollen, an ovule, an ambryo, a petiole, a shoot or a part thereof, a stem or a part thereof, a root or a part thereof, a root tip, a cutting, a seed, a part of a seed, seedcoat or another maternal tissue which is part of a seed grown on NUN 7206 ON, hypocotyl, cotyledon, a pistil, an anther, and a flower or a part of any of these and the like. Also any developmental stage is included, such as seedlings, cuttings prior or after rooting, mature plants or leaves. Alternatively, a plant part may also include a plant seed which comprises one or two sets of chromosomes derived from the parent plant.

By "bulb" or "onion bulb" is meant the (commercially) (harvested or harvestable) edible portion of the onion plant. An onion bulb comprises an apex and concentric, enlarged fleshy leaf bases, also called fleshy scale leaves. Onion bulbs may be developing onion bulbs or mature onion bulbs. A small bulb or a bulb early in its development or a secondary bulb developing on the main bulb may be described as a bulblet.

"Harvested plant material" refers herein to plant parts (e.g. bulbs detached from the whole plant) which have been collected for further storage and/or further use.

"Harvested seeds" refers to seeds harvested from a line or variety, e.g. produced after self-fertilization or cross-fertilization and collected.

"REFERENCE VARIETY" refers to the variety Calibra from company Bejo B.V., which has been planted in a trial together with NUN 7206 ON. USDA descriptors of NUN 7206 ON were compared to the USDA descriptors of Calibra.

A plant having "all the physiological and morphological characteristics" of a referred-to-plant means a plant having the physiological and morphological characteristics of the referred-to-plant when grown under the same environmental conditions, preferably in the same experiment; the referred-to-plant can be a plant from which it was derived, e.g. the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 and/or 2 and/or 3 or "all or all but one, two or three of the physiological and morphological characteristics" of Table 1 and/or 2 and/or 3

For NUN 7206 ON the distinguishing characteristics are 1) average bulb diameter; 2) average plant height; 3) average leaf length; 4) typical bulb scale retention; 5) typical leaf bloom; 6) average column height; 7) average column height; 8) average scape length; 9) average scape diameter; and 10) average bulb weight.

In certain embodiments the plant of the invention has all the physiological and morphological characteristics, except for certain characteristics mentioned, e.g. the characteristic(s) derived from a converted or introduced gene or trait and/or except for the characteristics which differ, for example a Single Locus Conversion.

In one embodiment, the invention relates to a Single Locus Converted plant of NUN 7206 ON.

Similarity between different plants is defined as the number of morphological and/or physiological characteristics (or the characteristics as listed in Table 1 and/or 2 and/or 3 that are the same between the two plants that are compared when grown under the same environmental conditions. Numerical characteristics are considered "the same" when the value for a numeric characteristic is evaluated at significance levels of 1%, 5% or 10% significance level, or at p≤0.05 using one way Analysis of variance (ANOVA), a standard methods known to the skilled person. Non-numerical or "type" characteristic are considered "the same" if identical or having the same value when scored for USDA and/ or UPOV descriptors, if the plants are grown under the same conditions.

"Distinguishing characteristics" or "distinguishing morphological and/or physiological characteristics" refers herein the characteristics which are distinguishing between NUN 7206 ON and other onion varieties, such as Calibra, when grown under the same environmental conditions, especially the following characteristics: 1) average bulb diameter; 2) average plant height; 3) average leaf length; 4)typical bulb scale retention; 5) typical leaf bloom; 6) average column height; 7) average column height; 8) average scape length; 9) average scape diameter; and 10) average bulb weight. In one aspect, the distinguishing characteristics further include at least one, two, three or more (or all) of the characteristics listed in Table 1 and/or 2 and/or 3. All numerical distinguishing characteristics are statistically significantly different at $p<0.05$.

Thus, an onion plant "comprising the distinguishing characteristics of "NUN 7206 ON" refers herein to an onion plant which does not differ significantly from NUN 7206 ON in characteristics 1) to 5) above. In a further aspect the onion plant further does not differ significantly from NUN 7206 ON in one or more, or all characteristics 6) to 10) as mentioned above. In yet a further aspect the onion plant further does not differ in all or all but one, two, three, four, five or six characteristics listed in Table 1 and/or 2 and/or 3. In still another aspect the onion plant does not differ in any of the distinguishing characteristics 1) to 10) listed above.

The physiological and/or morphological characteristics mentioned above are commonly evaluated at significance levels of 1%, 5% or 10% or evaluated at $p<0.05$ using ANOVA, when measured under the same environmental conditions. For example, a progeny plant of NUN 7206 ON may have one or more (or all) of the essential physiological and/or morphological characteristics of NUN 7206 ON listed in Table 1 and/or 2 and/or 3, as determined at the 5% significance level when grown under the same environmental conditions.

As used herein, the term "variety", "cultivated onion" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

"Plant line" is for example a breeding line which can be used to develop one or more varieties. Progeny obtained by selfing a plant line has the same phenotype as its parents.

"Hybrid variety" or "F1 hybrid" refers to the seeds harvested from crossing two inbred (nearly homozygous) parental lines. For example, the female parent is pollinated with pollen of the male parent to produce hybrid (Fl) seeds on the female parent.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) a bulb, a harvested bulb, a part of a bulb, a bulblet, a harvested bulblet, a part of a bulblet, a scale, a part of a scale, a leaf, a part of a leaf, pollen, an ovule, a cell, a petiole, a shoot or a part thereof, a stem or a part thereof, a root or a part thereof, a root tip, a cutting, a seed, hypocotyl, cotyledon, a pistil, an anther, and a flower or a part thereof, etc. When a whole plant is regenerated by vegetative propagation, it is also referred to as a vegetative propagation.

"Selfing" refers to self-pollination of a plant, i.e., the transfer of pollen from the anther to the stigma of the same plant.

"Crossing" refers to the mating of two parent plants. The term encompasses "cross-pollination" and "selfing".

"Cross-pollination" refers to the fertilization by the union of two gametes from different plants.

"Planting" or "planted" refers to seeding (direct sowing) or transplanting seedlings (plantlets) into a field by machine or hand.

"Yield" means the total weight of all onion bulbs harvested per surface unit or per plant of a particular line or variety. It is understood that "yield" expressed as weight of all onion bulbs harvested per hectare can be obtained by multiplying the number of plants per hectare times the "yield per plant".

"Marketable yield" means the total weight of all marketable onion bulb harvested per hectare of a particular line or variety, i.e. bulbs suitable for being sold for fresh consumption, having acceptable shape, moisture, pungency etc., and no or very low levels of deficiencies.

As used herein, the terms "resistance" and "tolerance" are used interchangeably to describe plants that show no symptoms or significantly reduced symptoms to a specified biotic pest, pathogen, abiotic influence or environmental condition. These terms are also used to describe plants showing some symptoms but that are still able to produce marketable product with an acceptable yield.

"Locus" (plural loci) refers to the specific location, place or site of a DNA sequence on a chromosome, where, for example, a gene or genetic marker is found. A locus may confer a specific trait.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

"Genotype" refers to the genetic composition of a cell or organism.

"Phenotype" refers to the detectable characteristics of a plant, cell or organism, which characteristics are the manifestation of gene expression.

Haploid" refers to a cell or organism having one set of the two sets of chromosomes in a diploid.

"Diploid" refers to a cell or organism having two sets of chromosomes.

"Maturity" refers to the development stage of an onion bulb when said onion bulb has fully developed (reached its final size). In particular embodiments "maturity" is defined as the mature state of bulb development and optimal time for harvest. Typically, maturity of a bulb is reached when the vegetative phase of an onion plant is over and leaves and neck of the onion plant dry out. As used herein, a "mature onion bulb" refers to any onion bulb that is ready for harvest. Generally, when 25-50% of the onion leaf tops have fallen over, the onion is ready for harvest.

"Harvest maturity" is referred to as the stage at which an onion bulb is ready for harvest or the optimal time to harvest the bulb. In one embodiment, harvest maturity is the stage where 25-50% of the onion leaf tops have fallen over.

"Flavor" refers to the sensory impression of a food or other substance, especially onion bulb or bulb part and is determined mainly by the chemical senses of taste and smell. Flavor is influenced by texture properties and by volatile and/or non-volatile chemical components (organic acids, lipids, carbohydrates, etc.). Pungency and sweetness are non-limiting examples of flavor components of an onion bulb.

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one onion line or variety to another. It optionally includes epigenetic modifications.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant".

"Progeny" as used herein refers to a plant derived from a plant designated NUN 7206 ON. A progeny may be derived by regeneration of cell culture or tissue culture or parts of a plant designated NUN 7206 ON or selfing of a plant designated NUN 7206 ON or by producing seeds of a plant designated NUN 7206 ON. In further embodiments, progeny may also encompass plants derived from crossing of at least one plant designated NUN 7206 ON with another onion plant of the same or another variety or (breeding) line, or wild onion plants, backcrossing, inserting of a locus into a plant or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above.

The terms "gene converted" or "conversion plant" in this context refer to onion plants which are developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of a onion variety are recovered in addition to the characteristics of the single locus having been transferred into the variety via the backcrossing technique and/or by genetic transformation.

"Transgene" or "chimeric gene" refers to a genetic locus comprising a DNA sequence which has been introduced into the genome of a onion plant by transformation. A plant comprising a transgene stably integrated into its genome is referred to as "transgenic plant".

"Linkage" refers to a phenomenon wherein alleles on the same chromosome tend to segregate together more often than expected by chance if their transmission was independent.

"Marker" refers to a readily detectable phenotype, preferably inherited in codominant fashion (both alleles at a locus in a diploid heterozygote are readily detectable), with no environmental variance component, i.e., a heritability of 1.

"Average" refers herein to the arithmetic mean.

"Substantially equivalent" refers to a characteristic that, when compared, does not show a statistically significant difference (e.g., p=0.05) from the mean.

The term "mean" refers to the arithmetic mean of several measurements. The skilled person understands that the appearance of a plant depends to some extent on the growing conditions of said plant. Thus, the skilled person will know typical growing conditions for onions described herein. The mean, if not indicated otherwise within this application, refers to the arithmetic mean of measurements on at least 10 different, randomly selected plants of a variety or line.

DETAILED DESCRIPTION

The present invention relates to a *Allium cepa* variety, referred to as NUN 7206 ON, which—when compared to check variety Calibra—has a 1) average bulb diameter; 2) average plant height; 3) average leaf length; 4) typical bulb scale retention; 5) typical leaf bloom; 6) average column height; 7) average column height; 8) average scape length; 9) average scape diameter; and 10) average bulb weight. Also encompassed by the present invention are progeny plants having all but 1, 2, or 3 of the morphological and/physiological characteristics of NUN 7206 ON and methods of producing plants in accordance with the present invention.

A onion plant of NUN 7206 ON differs from the most similar reference variety Calibra in one or more characteristics (referred herein to as "distinguishing characteristics" or "distinguishing morphological and/or physiological characteristics" (or essential physiological and/or morphological characteristics) selected from: 1) average bulb diameter; 2) average plant height; 3) average leaf length; 4) typical bulb scale retention; 5) typical leaf bloom; 6) average column height; 7) average column height; 8) average scape length; 9) average scape diameter; and 10) average bulb weight.

It is understood that "significant" differences refer to statistically significant differences, when comparing the characteristic between two plant lines or varieties when grown under the same conditions. Preferably at least about 10, 15, 20, 50 or more plants per line or variety are grown under the same conditions (i.e. side by side) and characteristics are measured on at least about 10, 15, 20 or more randomly selected plant or plant parts to obtain averages. Thus, physiological and morphological characteristics or traits are commonly evaluated at a significance level of 1%, 5% or 10% or evaluated at p≤0.05 using ANOVA, when measured in plants grown under the same environmental conditions.

Thus, in one aspect, the invention provides a seed of the onion variety designated NUN 7206 ON wherein a representative sample of seeds of said variety was deposited under the Budapest Treaty, with Accession number NCIMB 42143.

In another aspect, the invention provides for a onion plant of variety NUN 7206 ON, a representative sample of seed from said variety has been deposited under the Budapest Treaty, with Accession number NCIMB 42143.

A seed of NUN 7206 ON is obtainable by crossing the male parent of NUN 7206 ON with the female parent of NUN 7206 ON and harvesting the seeds produced on the female parent. The resultant NUN 7206 ON seeds can be grown to produce NUN 7206 ON plants. In one embodiment a seed or a plurality of seeds of NUN 7206 ON are packaged into containers of any size or type (e.g., bags, cartons, cans, etc.). The seed may be disinfected, primed and/or treated with various compounds, such as seed coatings or crop protection compounds.

Also provided is a plant of onion variety NUN 7206 ON, or a bulb or other plant part thereof, produced from a seed, wherein a representative sample of said seeds has been deposited under the Budapest Treaty, with Accession Number NCIMB 42143. Also included is a cell culture or tissue culture produced from such a plant.

In one embodiment the invention provides a onion plant regenerated from the tissue or cell culture of NUN 7206 ON, wherein the plant has all or all but one, two or three of of the physiological and morphological characteristics of NUN 7206 ON as listed in Table 1 and/or 2 and/or 3 when determined at the 5% significance level or evaluated at p≤0.05 using ANOVA. In another embodiment, the invention provides a onion plant regenerated from the tissue or cell culture of NUN 7206 ON, wherein the plant has all or all but one, two or three of the physiological and morphological characteristics of NUN 7206 ON when determined at the 5% significance level or evaluated at p≤0.05 using ANOVA.

Plants of NUN 7206 ON can be produced by seeding directly in the ground (e.g., field) or by germinating the seeds in controlled environment conditions (e.g., greenhouses) and then transplanting the seedlings into the field. For example, the seed can be sown into prepared seed beds where they will remain for the entire production of the crop. Alternatively, the onion seed may be planted or transplanted in prepared mounds.

In other aspects, the invention provides for a bulb of onion variety NUN 7206 ON, or a plant part, such as pollen, flowers, shoots or cuttings of variety NUN 7206 ON or parts thereof.

In one embodiment any plant of the invention comprises at least 3, 4, 5 or more, e.g. 6, 7, 8, 9 or all of the following morphological and/or physiological characteristics (i.e. distinguishing characteristics (average values; measured at harvest or market maturity, as indicated on the USDA Objective description of variety—Onion (unless indicated otherwise), when grown under the same environmental conditions): 1) average bulb diameter; 2) average plant height; 3) average leaf length; 4)typical bulb scale retention; 5) typical leaf bloom; 6) average column height; 7) average column height; 8) average scape length; 9) average scape diameter; and 10) average bulb weight.

In still another aspect the invention provides a method of producing an onion plant, comprising crossing a plant of onion variety NUN 7206 ON with a second onion plant one or more times, and selecting progeny from said crossing. In one embodiment of the invention, the first step in "crossing" comprises planting seeds of a first and a second parent onion plant, often in proximity so that pollination will occur for example, mediated by insect vectors. Alternatively, pollen can be transferred manually. Where the plant is self-pollinated, pollination may occur without the need for direct human intervention other than plant cultivation.

In yet another aspect the invention provides a method of producing a onion plant, comprising selfing a plant of onion variety NUN 7206 ON one or more times, and selecting progeny from said selfing.

In other aspects, the invention provides for a progeny of variety NUN 7206 ON such as progeny obtained by further breeding NUN 7206 ON. Further breeding NUN 7206 ON includes selfing NUN 7206 ON one or more times and/or cross-pollinating NUN 7206 ON with another onion plant or variety one or more times. In particular, the invention provides for progeny that retain all the essential morphological and physiological characteristics of NUN 7206 ON or that retain one or more of the distinguishing characteristics of the onion type described further above and when grown under the same environmental conditions. In another aspect, the invention provides for a vegetative reproduction of the variety and a plant having all but 1, 2, or 3 of the physiological and morphological characteristics of NUN 7206 ON (e.g. as listed in Table 1 and/or 2 and/or 3).

The morphological and/or physiological differences between a plant according to the invention, i.e. NUN 7206 ON or progeny thereof, or a plant having all but 1, 2, or 3 of the physiological and morphological characteristics of NUN 7206 ON (as listed in Table 1 and/or 2 and/or 3); and another known variety can easily be established by growing NUN 7206 ON next to the other variety (in the same field, under the same environmental conditions), preferably in several locations which are suitable for said onion cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA. In an onion trial, maturity, leaf shape, leaf color, flower size and color, bulb type, bulb color, bulb size, bulb shape, onion sweetness and pungency, disease resistance, insect resistance, can be measured and directly compared for species of *Allium cepa*.

The morphological and physiological characteristics (and the distinguishing characteristics) of NUN 7206 ON are provided in the Examples, in Table 1 and/or 2 and/or 3. Encompassed herein is also a plant derivable from NUN 7206 ON (e.g. by selfings and/or crossing and/or backcrossing with NUN 7206 ON and/or progeny thereof) comprising all or all but one, two or three of the physiological and morphological characteristics of NUN 7206 ON listed in Table 1 and/or 2 and/or 3 as determined at the 5% significance level or evaluated at p≤0.05 using ANOVA when grown under the same environmental conditions and/or comprising one or more (or all; or all except one, two or three) of the distinguishing characteristics as determined at the 5% significance level when grown under the same environmental conditions.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World Wide Web at rhs.org.uk/Plants/RHS-Publications/RHS-colour-charts).

In a preferred embodiment, the invention provides for a onion bulb of variety NUN 7206 ON, or a part of said bulb.

In another embodiment, the invention provides for a container comprising or consisting of a plurality of harvested onion bulbs or parts of bulbs of NUN 7206 ON, or bulbs of progeny thereof, or bulbs of a derived variety.

In yet a further embodiment, the invention provides for a method of producing a new onion plant. The method comprises crossing a plant of the invention NUN 7206 ON, or a plant comprising all but 1, 2, or 3 of the morphological and physiological characteristics of NUN 7206 ON (as listed in Table 1 and/or 2 and/or 3), or a progeny plant thereof, either as male or as female parent, with a second onion plant (or a wild relative of onion) one or more times, and/or selfing a onion plant according to the invention i.e. NUN 7206 ON, or a progeny plant thereof, one or more times, and selecting progeny from said crossing and/or selfing. The second onion plant may for example be a line or variety of the species *Allium cepa* or other *Allium* species.

Progeny are either the generation (seeds) produced from the first cross (F1) or selfing (S1), or any further generation produced by crossing and/or selfing (F2, F3, etc.) and/or backcrossing (BC1, BC2, etc.) one or more selected plants of the F1 and/or S1 and/or BC1 generation (or plants of any further generation, e.g. the F2) with another onion plant (and/or with a wild relative of onion). Progeny may have all the physiological and morphological characteristics of onion variety NUN 7206 ON when grown under the same environmental conditions and/or progeny may have (be selected for having) one or more of the distinguishing characteristics of onion of the invention. Using common breeding methods such as backcrossing or recurrent selection, one or more specific characteristics may be introduced into NUN 7206 ON, to provide or a plant comprising all but 1, 2, or 3 or more of the morphological and physiological characteristics of NUN 7206 ON (as listed in Table 1 and/or 2 and/or 3).

The invention provides for methods of producing plants which retain all the morphological and physiological characteristics of NUN 7206 ON. The invention provides also for methods of producing a plant comprising all but 1, 2, or 3 or more of the morphological and physiological characteristics of NUN 7206 ON (e.g. as listed in Table 1 and/or 2 and/or 3), but which are still genetically closely related to NUN 7206 ON. The relatedness can, for example be determined by fingerprinting techniques (e.g., making use of isozyme markers and/or molecular markers such as SNP markers, AFLP markers, microsatellites, minisatellites, RAPD markers, RFLP markers and others). A plant is "closely related" to NUN 7206 ON if its DNA fingerprint is at least 80%, 90%, 95% or 98% identical to the fingerprint of NUN 7206 ON. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Ince et al., (2010) Biochem. Genet. 48:83-95). The invention also provides a plant and a variety obtained by these methods. Plants may be produced by crossing and/or selfing, or alternatively, a plant may simply be identified and selected amongst NUN 7206 ON plants, or progeny thereof, e.g. by identifying a variant within NUN 7206 ON or progeny thereof (e.g. produced by selfing) which variant differs from NUN 7206 ON in one, two or three of the morphological and/or physiological characteristics (e.g. in one, two or three distinguishing characteristics), e.g. those listed in Table 1 and/or 2 and/or 3 or others. In one embodiment the invention provides an onion plant having a Jaccard's Similarity index with NUN 7206 ON of at least 0.8, e.g. at least 0.85, 0.9, 0.95, 0.98 or even at least 0.99.

The present invention also provides a onion seed and a plant produced by a process that comprises crossing a first parent onion plant with a second parent onion plant, wherein at least one of the first or second parent onion plants is a plant provided herein, such as from variety NUN 7206 ON. In another embodiment of the invention, onion seed and plants produced by the process are first filial generation (F1) onion seed and plants produced by crossing a plant in accordance with the invention with another, distinct plant.

The present invention further contemplates plant parts of such an F1 onion plant, and methods of use thereof. Therefore, certain exemplary embodiments of the invention provide an F1 onion plant and seed thereof.

WO2013182646 which is incorporated by reference, relates to a non-destructive method for analyzing maternal DNA of a seed. In this method the DNA is dislodged from the seed coat surface and can be used to collect information on the genome of the maternal parent of the seed. This method for analyzing maternal DNA of a seed, comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of NUN 7206 ON (i.e. is progeny of NUN 7206 ON), because the seed coat is genetically identical to NUN 7206 ON. In one embodiment, the present invention relates to a seed coat comprising maternal tissue of NUN 7206 ON. In another embodiment the invention relates to a onion seed comprising a seed coat that comprises maternal tissue from NUN 7206 ON.

By crossing and/or selfing also (one or more) single traits may be introduced into the variety of the invention i.e. NUN 7206 ON (e.g., using backcrossing breeding schemes), while retaining the remaining morphological and physiological characteristics of NUN 7206 ON and/or while retaining one or more distinguishing characteristics. A single trait converted plant may thereby be produced. For example, disease resistance genes may be introduced, genes responsible for one or more quality traits, yield, etc. Both single genes (dominant or recessive) and one or more QTLs (quantitative trait loci) may be transferred into NUN 7206 ON by breeding with NUN 7206 ON.

Alternatively, a single trait converted plant or single locus converted plant may be produced by the following steps
 a. obtaining a cell or tissue culture of cells of NUN 7206 ON;
 b. genetically transforming or mutating said cells;
 c. growing the cells into a plant; and
 d. optionally selecting a plant that contains the desired single locus conversion The skilled person is familiar with various techniques for genetically transforming a single locus in a plant cell, or mutating said cells.

Any pest or disease resistance genes may be introduced into a plant according to the invention, i.e. NUN 7206 ON, progeny thereof or into a plant comprising all but 1, 2, or 3 or more of the morphological and physiological characteristics of NUN 7206 ON (e.g. as listed in Table 1 and/or 2 and/or 3). Resistance to one or more of the following diseases is preferably introduced into plants of the invention: Cucumber Mosaic Virus, Curly Top Virus, Onion Mottle Virus, Potato Y Virus, Blotchey Ripening, Tobacco Etch Virus, the various Tobacco Mosaic Virus races, Concentric cracking, Onion spotted wilt, Onion yellows, Gold Fleck, Bacterial canker, Bacterial soft rot, Bacterial speck, Bacterial wilt, Anthracnose (*Gloeosporium piperatum*), Fusarium wilt (*F. oxysporum* races), *Alternaria*, Bacterial Spot (*Xanthomonas vesicatoria*), Nematode (*Meloidogyne* spp), Late blight (*Phytophthora infestans* races), Leaf mold (*Cladosporium fulvum* races), Colorado potato beetle, Spider mites, Whitefly and Verticillium Wilt (*Verticillium dahliae*). Other resistance genes, against pathogenic viruses, fungi, bacteria, nematodes, insects or other pests may also be introduced.

Thus, invention also provides a method for developing a onion plant in a onion breeding program, using a onion plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 7206 ON or progeny thereof, or a plant comprising all but 1, 2, or 3 or more of the morphological and physiological characteristics of NUN 7206 ON (e.g. as listed in Table 1 and/or 2 and/or 3), with a different onion plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Vidaysky and Czosnek, (1998) Phytopathology 88(9): 910-4). For breeding methods in general see Principles of Plant Genetics and Breeding, 2007, George Acquaah, Blackwell Publishing, ISBN-13: 978-1-4051-3646-4.

The invention also provides a onion plant comprising at least a first set of the chromosomes of onion variety NUN 7206 ON, a sample of seed of said variety having been deposited under Accession Number NCIMB 42143; optionally further comprising a single locus conversion, wherein said plant has essentially all of the morphological and physiological characteristics of the plant comprising at least a first set of the chromosomes of onion NUN 7206 ON. In another embodiment, this single locus conversion confers a trait selected from the group consisting of male sterility, herbicide tolerance, pathogen resistance (e.g., insect resistance, nematode resistance, resistance to bacterial, fungal, and viral disease), environmental stress tolerance, modified carbohydrate metabolism, modified protein metabolism improved harvest characteristics, enhanced nutritional quality, increased antioxidant content, improved processing characteristics, high yield, improved characteristics related to the bulb flavor, texture, size, shape, durability, shelf life, and yield, increased soluble solids content, uniform ripening, delayed or early ripening, adaptability for soil conditions, and adaptability for climate conditions In one embodiment, NUN 7206 ON may also be mutated (by e.g. irradiation, chemical mutagenesis, heat treatment, etc.) and mutated seeds or plants may be selected in order to change one or more characteristics of NUN 7206 ON. Methods such as TILLING may be applied to onion populations in order to identify mutants. Similarly, NUN 7206 ON may be transformed and regenerated, whereby one or more chimeric genes are introduced into the variety or into a plant comprising all but 1, 2, 3, or more of the morphological and physiological characteristics (e.g. as listed in Table 1 and/or 2 and/or 3). Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 7206 ON, or progeny thereof, by transforming NUN 7206 ON or progeny thereof with a transgene that confers the desired trait, wherein the transformed plant retains all the phenotypic and/or morphological and/or physiological characteristics of NUN 7206 ON or the progeny thereof and contains the desired trait.

The invention also provides a plant having one, two or three physiological and/or morphological characteristics which are different from those of NUN 7206 ON and which otherwise has all the physiological and morphological characteristics of NUN 7206 ON, wherein a representative sample of seed of variety NUN 7206 ON has been deposited under Accession Number NCIMB 42143. In particular variants which differ from NUN 7206 ON in none, one, two or three of the characteristics mentioned in Table 1 and/or 2 and/or 3 are encompassed.

In one aspect, the the plant having one, two or three physiological and/or morphological characteristics which are different from those of NUN 7206 ON and which otherwise has all the physiological and morphological characteristics of NUN 7206 ON differs from NUN 7206 ON in one, two or three of the distinguishing morphological and/or physiological characteristics selected from a 1) average bulb diameter; 2) average plant height; 3) average leaf length; 4)typical bulb scale retention; 5) typical leaf bloom; 6) average column height; 7) average column height; 8) average scape length; 9) average scape diameter; and 10) average bulb weight.

In another embodiment the plant having one, two or three physiological and/or morphological characteristics which are different from those of NUN 7206 ON and which otherwise has all the physiological and morphological characteristics of NUN 7206 ON may differ from NUN 7206 ON in one, two or three morphological or physiological characteristic other than the "distinguishing morphological and/or physiological characteristics" (or essential physiological and/or morphological characteristics) of NUN 7206 ON selected from: a 1) average bulb diameter; 2) average plant height; 3) average leaf length; 4) typical bulb scale retention; 5) typical leaf bloom; 6) average column height; 7) average column height; 8) average scape length; 9) average scape diameter; and 10) average bulb weight.

Onions according to the invention, such as the variety NUN 07206 ONLNUN 7206 ON, or its progeny, or a plant having all physiological and/or morphological characteristics but one, two or three which are different from those of NUN 7206 ON, can also be reproduced using vegetative reproduction methods. Therefore, the invention provides for a method of producing plants, or a part thereof, of variety NUN 7206 ON, comprising vegetative propagation of variety NUN 7206 ON. Vegetative propagation comprises regenerating a whole plant from a plant part of variety NUN 7206 ON (or from its progeny or from or a plant having all physiological and/or morphological characteristics of NUN 7206 ON but one, two or three, which are different), such as a cutting, a cell culture or a tissue culture.

The invention also concerns methods of vegetatively propagating a plant of the invention. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets The invention also provides for a vegetatively propagated plant of variety NUN 7206 ON (or from its progeny or from or a plant having all but one, two or three physiological and/or morphological characteristics of NUN 7206 ON, or a part thereof, having one or more distinguishing characteristics and/or all the morphological and physiological characteristics of NUN 7206 ON (except for the characteristics differing), when grown under the same environmental conditions.

A parts of NUN 7206 ON (or of its progeny or of a plant having all physiological and/or morphological characteristics but one, two or three which are different from those of NUN 7206 ON) encompasses any cells, tissues, organs obtainable from the seedlings or plants, such as but not limited to: an onion bulb or a part thereof, a cutting, hypocotyl, cotyledon, seedcoat, pollen and the like. Such parts can be stored and/or processed further. Encompassed are therefore also food or feed products comprising one or more of such parts, such as canned, chopped, cooked, roasted, fried, in a sauce, in a sandwich, pasted, puréed or concentrated, juiced, frozen, dried, pickled, or powdered onion bulb from NUN 7206 ON or from progeny thereof, or from a derived variety, such as a plant having all but one, two or three physiological and/or morphological characteristics of NUN 7206 ON.

In one aspect a haploid plant and/or a double haploid plant of NUN 7206 ON, or a plant having all but one, two or three physiological and/or morphological characteristics of NUN 7206 ON, or progeny of any of these, are encompassed herein. Haploid and double haploid (DH) plants can, for example, be produced by cell or tissue culture and chromosome doubling agents and regeneration into a whole plant. For DH production chromosome doubling may be induced using known methods, such as colchicine treatment or the like.

In yet another aspect haploid plants and/or double haploid plants derived from NUN 7206 ON that, when combined, make a set of parents of NUN 7206 ON are encompassed herein.

Using methods known in the art like "reverse breeding", it is possible to produce parental lines for a hybrid plant such as NUN 7206 ON; where normally the hybrid is produced from the parental lines. Such methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Nature Protocols Volume: 9, Pages: 761-772 (2014) DOI: doi:10.1038/nprot.2014.049, which are enclosed by reference. Such method for producing parental lines for a hybrid organism, comprises the steps of: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B) ; d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 7206 ON) comprising the step of making double haploid cells from haploid cells from the plant of the invention (NUN 7206 ON) or a seed of that plant; and optionally crossing these parental lines to produce and collect seeds. In another aspect, the invention relates to a combination of parental lines produced by this method. In still another aspect said combination of parental lines can be used to produce a seed or plant of NUN 7206 ON when these parental lines are crossed. In still another aspect, the invention relates to a combination of parental lines from which a seed or plant having all physiological and/or of NUN 7206 ON morphological characteristics but one, two or three which are different can be produced or in another aspect, wherein a seed or plant having the distinguishing characteristics 1) -5) or 1)-10) of NUN 7206 ON, as herein defined, can be produced when grown under the same environmental conditions. In still another aspect, the invention relates to a combination of parental lines from which a seed or plant having all the characteristics of NUN 7206 ON as defined in Table 1 and/or 2 and/or 3 when grown under the same conditions can be produced.

In another alternative aspect, the invention provides a method of introducing a single locus conversion or single trait conversion or a desired trait into NUN 7206 ON comprising:
  a. obtain a combination of a male and a female parental line of NUN 7206 ON,
  b. introduce a single locus conversion in at least one of the parents of step a;
  c. crossing the converted parent with the other parent of step a to obtain seed of NUN 7206 ON
  A combination of a male and a female parental line of NUN 7206 ON can be generated by methods described herein, for example through reverse breeding;
  Step b) of the above method—introduce a single locus conversion in at least one of the parents of step a—may be done through the following method:
    i. obtaining a cell or tissue culture of cells of the parental line of NUN 7206 ON;
    ii. genetically transforming or mutating said cells;
    iii. growing the cells into a plant; and
    iv. optionally selecting plants that contain the single locus conversion, the single trait conversion or the desired trait.
  Step b) of the above method - introduce a single locus conversion in at least one of the parents of step a—may be done through the following method:
    i. crossing the parental line of NUN 7206 ON with a second onion plant comprising the single locus conversion, the single trait conversion or the desired trait;
    ii. selecting Flprogeny plants that contain the single locus conversion, the single trait conversion or the desired trait;
    iii. crossing said selected progeny plants of step ii with the parental line of step i, to produce a backcross progeny plant;
    iv. selecting backcross progeny plants comprising the single locus conversion, the single trait conversion or the desired trait and otherwise all or all but one, two or three of the morphological and physiological characteristics the parental line of step i to produce selected backcross progeny plants; and
    v. optionally repeating steps iii and iv one or more times in succession to produce selected second, third or fourth or higher backcross progeny plants comprising the single locus conversion, the single trait conversion or the desired trait and otherwise all or all but one, two or three of the morphological and physiological characteristics the parental line of step i to produce selected backcross progeny plants, when grown in the same environmental conditions.

The invention further relates to plants obtained by this method.

The above method is provided, wherein the single locus conversion concerns a trait, wherein the trait is pest resistance or disease resistance.

In one embodiment the trait is disease resistance and the resistance is conferred to Cucumber Mosaic Virus, Curly Top Virus, Onion Mottle Virus, Potato Y Virus, Blotchey Ripening, Tobacco Etch Virus, the various Tobacco Mosaic Virus races, Concentric cracking, Onion spotted wilt, Onion yellows, Gold Fleck, Bacterial canker, Bacterial soft rot, Bacterial speck, Bacterial wilt, Anthracnose (*Gloeosporium piperatum*), Fusarium wilt (*F. oxysporum* races), Alternaria, Bacterial Spot (*Xanthomonas vesicatoria*), Nematode (*Meloidogyne incognita*), Late blight (*Phytophthora infestans* races), Leaf mold (*Cladosporium fulvum* races), Colorado potato beetle, Spider mites, Whitefly and Verticillium Wilt (*Verticillium dahliae*).

Also provided are plant parts derived from variety NUN 7206 ON (or from its progeny or from a plant having all but one, two or three physiological and/or morphological characteristics which are different from those of NUN 7206 ON, or from a vegetatively propagated plant of NUN 7206 ON (or from its progeny or from a plant having all but one, two or three physiological and/or morphological characteristics which are different from those of NUN 7206 ON), being selected from the group consisting of a bulb, a harvested bulb, a part of a bulb, a bulblet, a harvested bulblet, a part of a bulblet, a scale, a part of a scale, a leaf, a part of a leaf, pollen, an ovule, a cell, a petiole, a shoot or a part thereof, a stem or a part thereof, a root or a part thereof, a root tip, a cutting, a seed, a part of a seed, seedcoat or another maternal tissue which is part of a seed grown on NUN 7206 ON, hypocotyl, cotyledon, an anther, and a flower or a part thereof.

In one embodiment, the invention provides for extracts of a plant described herein and compositions comprising or consisting of such extracts. In a preferred embodiment, the extract consists of or comprises tissue of a plant described herein or is obtained from such tissue.

In still yet another aspect, the invention provides a method of determining the genotype of a plant of the invention comprising the step of detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLPI) of genomic DNA, random amplified polymorphic detection (RAPD) of genomic DNA, amplified fragment length polymorphism detection (AFLPD), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium The invention also provides for a food or feed product comprising or consisting of a plant part described herein wherein the plant part can be identified as a part of the plant of the invention. Preferably, the plant part is a onion bulb or part thereof and/or an extract from a bulb or another plant part described herein. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

For example, containers such as cans, boxes, crates, bags, cartons, Modified Atmosphere Packagings, films (e.g. biodegradable films), etc. comprising a plant or a parts of a plant (fresh and/or processed) described herein or a seed of NUN 7206 ON are also provided herein.

All documents (e.g., patent publications) are herein incorporated by reference in their entirety. Cited references:
U.S. Ser. No. 12/861,740
U.S. Ser. No. 12/020,360
Dunstan and Short (1977) Physiol, Plant, 41: 70-72
Pike and Yoo, Scientia Horticulturae, 45 (1990) 31-36)
"Guidelines for the Conduct of Tests for Distinctness, Uniformity and Stability", TG/46/7 (Geneva 2009, revised 2015), as published by UPOV (International Union for the Protection of New Varieties and Plants, available on the world wide web at upov.int) and which can be downloaded from the world wide web at edocs/tgdocs/en/tg046.pdf
US Department of Agriculture, Agricultural Marketing Service, Plant Variety Protection Office, Beltsville, Md. 20705 (available on the world wide web at ams usda.gov) and which can be downloaded from the world wide web at /sites/default/files/media/16-Onion.pdf.
Vos et al. 1995, Nucleic Acid Research 23: 4407-4414
Ince et al., (2010) Biochem. Genet. 48:83-95.
WO2013182646
Vidaysky and Czosnek, (1998) Phytopathology 88(9): 910-4
Principles of Plant Genetics and Breeding, 2007, George Acquaah, Blackwell Publishing, ISBN-13: 978-1-4051-3646-4.
WO2014076249
Nature Protocols Volume: 9, Pages: 761-772 (2014) DOI: doi:10.1038/nprot.2014.049

EXAMPLES

Development of NUN 7206 ON

The hybrid NUN 7206 ON was developed from a male and female proprietary inbred line of Nunhems. The female and male parents were crossed to produce hybrid (F1) seeds of NUN 7206 ON The seeds of NUN 7206 ON can be grown to produce hybrid plants and parts thereof (e.g. onion fruit). The hybrid NUN 7206 ON can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant concluded that NUN 7206 ON is uniform and stable.

Deposit Information

A total of 2500 seeds of the hybrid variety NUN 7206 ON were deposited according to the Budapest Treaty by Nunhems B.V. on May 8, 2013, at the NCIMB Ltd., Ferguson Building, Craibstone Estate, Bucksburn, Aberdeen AB21 9YA, United Kingdom (NCIMB). The deposit has been assigned NCIMB number 42143. A deposit of NUN 7206 ON and of the male and female parent line is also maintained at Nunhems B.V. Access to the deposit will be available during the pendency of this application to persons determined by the Director of the U.S. Patent Office to be entitled thereto upon request. Subject to 37 C.F.R.§ 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The most similar variety to NUN 7206 ON is referred to as REFERENCE VARIETY, a variety from Bejo B.V. with the commercial name Calibra. In Table 1 a comparison between NUN 7206 ON and Calibra is shown based on a trial in the USA. Trial location: N46.08258, W119.46304, elevation 1275 ft. Planting date: 25 Mar. 2014.

Two replications of 50 plants each, from which 15 plants or plant parts were randomly selected, were used to measure characteristics. In Table 1 the USDA descriptors of NUN 7206 ON (this application) and REFERENCE VARIETY Calibra are listed.

In accordance with one aspect of the present invention, there is provided a plant having the physiological and morphological characteristics of onion variety NUN 7206 ON as presented in Table 1.

TABLE 1

Comparison of USDA descriptors between varieties NUN 7206 ON and REFERENCE VARIETY Calibra

| USDA Descriptor | Application Variety NUN 7206 ON | REFERENCE VARIETY Calibra |
| --- | --- | --- |
| 1. TYPE: | | |
| 1 = Bulb 2 = Bunching | 1 | 1 |
| 1 = short day; 2 = long day | 2 | 2 |
| Adaptation range (degree mean latitude) | n.r. | n.r. |
| Maturity (days): 1 = early (75-90); 2 = medium (100-120); 3 = late (>130) | 2 | 2 |
| 2. PLANT: | | |
| Height above soil line to highest point of any foliage | 102.9 cm | 95.6 cm |
| Taller than comparison variety | 7.2 cm | — |
| Plant 1 = erect (Spartam Gem); 2 = intermediate; 3 = floppy (Epoch) | 1 | 1 |
| 3. LEAF: | | |
| Length (before maturity yellowing begins) | 85 cm | 77 cm |
| Width | 34 mm | 36 mm |
| Thickness (at mid-length of longest leaf) | 3 mm | 2.7 mm |
| Color: 1 = light green (Early Grano); 2 = medium green (Yellow Bermuda); 3 = blue green (Australian Brown U.C. No.1) | 3 | 2 |
| Color Chart Code (RHS Color Chart) | Greyed green 189A | Yellow green 147B |
| Bloom: 1 = none-glossy; 2 = light (Early Grano); 3 = medium (Crystal Wax); 4 = heavy (California Early Red) | 3 | 2 |
| 4. SHEATH: | | |
| Column length (height from soil line to base of lowest succulent leaf) | 11 cm | 9 cm |
| Diameter (at mid-length) | 20 mm | 24 mm |
| Scape: (From soil line to base of inflorescence) | 80 cm | 103 |
| Scape: (diameter at mid-length) | 18 mm | 25 mm |
| 5. INFLORESCENCE: | | |
| 6. BULB: | | |
| Average number bulbs per meter | NA | NA |
| Size (harvested): 1 = small (Red Creol); 2 = medium (Australian Brown U.C. No. 1); 3 = large (Early Grano) | 2 | 2 |
| Shape: 1 = Globe (White Sweet Spanish); 2 = Deep Globe (Abundance); 3 = Flt. Globe (Australian Brn. U.C. No. 1); 4 = Top Shape (Texas Grano 502); 5 = Deep Flat (Granex); 6 = Thick Flat (Ebenezer); 7 = Flat (Crystal Wax); 8 = Torpedo-Long Oval (Italian Red) | 1 | 1 |
| Height: | 8 cm | 7.6 cm |
| Diameter: | 9.3 cm | 9.0 cm |
| Shape Index | 0.86 | 0.84 |
| 1 = invaginate; 2 = evaginate | n.r. | n.r. |
| Color (skin): 01 = Brown (Australian Brn. U.C. No. 1); 02 = Purplish Red (Italian Red); 03 = Buff Red (Red Creole); 04 = Pinkish Yellow (Ebenezer); 05 = Brownish Yellow (Mt. Danvers); 06 = Deep Yellow (Brigham Yellow Globe); 07 = Medium Yellow (Early Yellow Globe); 08 = Pale Yellow (Yellow Bermuda); 09 = White (White Sweet Spanish); 10 = Other (Specify) _____ | 03 (RHS Greyed Orange 167A) | 03 (RHS Greyed Orange 164A) |
| Color (interior): 1 = Pink; 2 = Red; 3 = Purplish Red; 4 = White; 5 = Cream; 6 = Light Green-Yellow; 7 = Dark Green-Yellow | 6 | 6 |

TABLE 1-continued

Comparison of USDA descriptors between varieties NUN 7206 ON and REFERENCE VARIETY Calibra

| USDA Descriptor | Application Variety NUN 7206 ON | REFERENCE VARIETY Calibra |
|---|---|---|
| Scales: 1 = Few (Crystal Wax); 2 = Medium (Australian Brown U.C. No. 1); 3 = Many (Sweet Spanish) | n.r. | n.r. |
| Scales: 1 = Thick (Australian Brown U.C. No. 1); 2 = Medium (Red Creole); 3 = Thin (Crystal Wax) | n.r. | n.r. |
| Scale retention: 1 = Very Good (Australian Brn. U.S. No. 1); 2 = Good (Ebenezer); 3 = Fair (Red Wethersfield); 4 = Poor (Crystal Wax) | 2 | 1 |
| Pugence: 1 = Mild (Early Grano); 2 = Medium (Crystal Wax); 3 = Strong (White Creole) | 1 | 1 |
| Storage: 1 = Good (Ebenezer); 2 = Fair (Yellow Globe Danvers); 3 = Poor (Crystal Wax) | 1 | 1 |
| 7. DISEASE RESISTANCE 0 = not tested; 1 = susceptible 2 = resistant | | |
| 8. INSECT RESISTANT 0 = not tested; 1 = susceptible 2 = resistant | | |

Table 1 and 2 contain typical values. Values may vary due to environment. Other values that are substantially equivalent are also within the scope of the invention. N.A.=not applicable; n.r.=not recorded.

TABLE 2

Comparison of non-USDA descriptors between NUN 07206 ON and REFERENCE VARIETY Calibra

| Descriptor | Application Variety NUN 07206 ON | Reference Variety Calibra |
|---|---|---|
| Bulb weight in grams | 388.93 | 337.6 |

Table 1 and 2 contain typical values. Values may vary due to environment. Other values that are substantially equivalent are also within the scope of the invention. N.A.=not applicable; n.r.=not recorded.

Results for other trials wherein various UPOV descriptors of NUN 07206 ON (this application) have been recorded are shown in Table 3. These trials were done over several years in several locations.

| UPOV Descriptor | ApplicationVariety NUN 07206 ON | |
|---|---|---|
| Plant: number of leaves per pseudostem | 1 very few/3 few/5 medium/7 many/9 very many | 5 |
| Foliage: attitude | 1 erect/2 erect to semi-erect/3 semi-erect/4 semi-erect to horizontal/5 horizontal | 1 |
| Foliage: waxiness | 1 absent or very weak/3 weak/5 medium/7 strong/9 very strong | 7 |
| Foliage: intensity of green color | 1 very light/3 light/5 medium/7 dark/9 very dark | 7 |
| Foliage: cranking | 1 absent or very weak/2 intermediate/3 strong | 1 |
| Leaf: length | 1 very short/3 short/5 medium/7 long/9 very long | 5 |
| Leaf: diameter | 1 small/5 medium/7 large | 5 |
| Pseudostem: length (up to highest green leaf) | 3 short/5 medium/7 long | 5 |
| Pseudostem: diameter (at mid-point of length) | 1 small/5 medium/7 large | 5 |
| Seed-propagated varieties only: Bulb: Tendency to split into bulblets (with dry skin around each bulblet) | 1 absent or very weak/3 weak/5 medium/7 strong/9 very strong | 1 |
| Bulb: degree of splitting into bulblets (with dry skin around each bulblet) | 1 absent or very weak/3 weak/5 medium/7 strong/9 very strong | 1 |
| Bulb: size | 1 very small/3 small/5 medium/7 large/9 very large | 5 |

| UPOV Descriptor | ApplicationVariety NUN 07206 ON | |
| --- | --- | --- |
| Bulb: height | 1 very short/3 short/5 medium/7 fall/9 very tall | 5 |
| Bulb: diameter | 1 small/5 medium/7 large | 5 |
| Bulb: ratio height/diameter | 1 very small/3 small/5 medium/7 large/9 very large | 5 |
| Bulb/Bulblet: position of maximum diameter | 1 towards stem end/2 at middle/3 towards root end | 2 |
| Bulb/Bulblet: width of neck | 1 very narrow/3 narrow/5 medium/7 broad/9 very broad | 5 |
| Bulb/Bulblet: shape (in longitudinal section) | 1 elliptic/2 medium ovate/3 broad elliptic/4 circular/5 broad ovate/6 broad obovate/7 rhombic/8 transverse medium elliptic/9 transverse narrow elliptic | 5 |
| Onion varieties only: Bulb: shape of stem end (as for 18) | 1 depressed/2 flat/3 slightly raised/4 rounded/5 slightly sloping/6 strongly sloping | 3 |
| Bulb/Bulblet: shape of root end | 1 depressed/2 flat/3 round/4 weakly tapered/5 strongly tapered | 3 |
| Bulb/Bulblet: adherence of dry skin after harvest | 1 very weak/3 weak/5 medium/7 strong/9 very strong | 5 |
| Bulb/Bulblet: thickness of dry skin | 3 thin/5 medium/7 thick | 5 |
| Bulb/Bulblet: base color of dry skin | 1 white/2 grey/3 green/4 yellow/5 brown/6 pink/7 red | 4 |
| Excluding varieties with white dry skin: Bulb/Bulblet: intensity of base color of dry skin | 3 light/5 medium/7 dark | 5 |
| Bulb/Bulblet: hue of color of dry skin (in addition to base color) | 1 absent/2 greyish/3 greenish/4 yellowish/5 brownish/6 pinkish/7 reddish/8 purplish | 5 |
| Bulb/Bulblet: hue of coloration of epidermis of fleshy scales | 1 absent/2 greenish/3 reddish | 2 |
| Bulb/Bulblet: number of growing points per kg | 1 very low/3 low/5 medium/7 high/9 very high | 1 |
| Bulb/Bulblet: dry matter content in percentage | 1 very low/3 low/5 medium/7 high/9 very high % | 5<br>9-11 |
| Tendency to bolting in spring sown trials | 1 absent or very weak/3 weak/5 medium/7 strong/9 very strong | 3 |
| Time of beginning of bolting in spring sown trials | 3 early/5 medium/7 late | 7 |
| Time of harvest maturity for spring sown trials (foliage fall-over in 80% of plants) | 1 very early/3 early/5 medium/7 late/9 very late | 5: 112 days |
| | (±comparable with the variety) | Infinity |
| Time of sprouting during storage | 3 early/5 medium/7 late | 7 |
| Male sterility | 1 absent or very weak/2 weak/3 strong<br>% | 3<br>100 |
| Relative maturity of the variety | | 112 |
| Special conditions for the examination of the variety | 1 = YES; 2 = NO | 1 |
| if yes provide details | Best adapted to spring sowing at 45 degrees latitude. | |
| Day length conditions which favour full bulb development | 1 short day/2 semi short day/3 semi long day/4 long day | 4 |
| Suitability for storage | 1 none/2 short term/3 long term | 3 |
| Type | 1 onion set production/2 silver skinned/3 normal sowing onion/4 overwintering/5 other | 3 |
| Main use | 1 fresh market or garden/2 industrial processing | 1 |
| Main use 2 | 1 seed/2 forage/3 garden plant/4 pot plant/5 cut-flower/6 other | 6 |
| When 6 other please provide details | Commercial production of onion bulbs. | |
| Other information | 1 = YES; 2 = NO | 2 |

What is claimed is:

1. A whole plant, plant part, or seed of onion variety NUN 7206 ON, wherein a representative sample of said seed has been deposited under Accession Number NCIMB 42143.

2. The plant part of claim 1, wherein said plant part is a leaf, pollen, an ovule, a fruit, a scion, a cutting, flower, a bulb, a bulblet, a scale, or a part of any of these or a cell.

3. A maternal tissue of a seed grown on the plant of claim 1.

4. A whole onion plant which does not differ from the plant of claim 1 in any physiological or morphological characteristic when measured at the 5% significance level and when grown under the same conditions, or a part of said plant.

5. A tissue or cell culture of regenerable cells of the plant of claim 1.

6. The tissue or cell culture according to claim 5, comprising cells or protoplasts from a plant part of embryos, meristems, cotyledons, hypocotyl, pollen, leaves, anthers, roots, root tips, pistil, petiole, flower, fruit, bulbs, bulblets, scales, seed, stem or stalks.

7. A whole onion plant regenerated from the tissue or cell culture of claim 5, wherein the plant has all of the physiological and morphological characteristics of the plant of NUN 7206 ON, wherein a representative sample of seed of said variety has been deposited under Accession Number NCIMB 42143, when determined at the 5% significance level, or a part of said plant.

8. A method for producing the plant of claim 1, or a part thereof, said method comprising vegetative propagation of a part of the plant of claim 1, wherein said part is a cell culture, or a tissue culture.

9. The method of claim 8, wherein said vegetative propagation comprises regenerating a whole plant from a part of NUN 7206 ON, wherein a representative sample of seed of said variety has been deposited under Accession Number NCIMB 42143.

10. A vegetative propagated plant, or a part thereof, wherein the plant has all of the physiological and morphological characteristics of the plant of claim 1 when grown under the same conditions determined at the 5% significance level.

11. A method of producing an onion plant, said method comprising crossing the plant of claim 1 with a second onion plant one time, and selecting progeny from said crossing for a desired phenotype and/or genotype and optionally allowing the progeny to form seed.

12. A food or feed product comprising the plant part of claim 2.

13. A method of producing double haploid plants comprising the step of making double haploid cells from haploid cells from the plant of claim 1 or a seed of claim 1.

14. A container comprising a whole plant, plant part, or seed of claim 1.

* * * * *